United States Patent
Gao et al.

(10) Patent No.: US 12,330,135 B2
(45) Date of Patent: Jun. 17, 2025

(54) COMPOSITE LAYER AGGLOMERATING ADSORBENT AND PREPARATION PROCESS THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Ningning Gao, Beijing (CN); Huiguo Wang, Beijing (CN); Yusi Liu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 749 days.

(21) Appl. No.: 17/596,943

(22) PCT Filed: Jun. 24, 2020

(86) PCT No.: PCT/CN2020/098147
§ 371 (c)(1),
(2) Date: Dec. 22, 2021

(87) PCT Pub. No.: WO2020/259595
PCT Pub. Date: Dec. 30, 2020

(65) Prior Publication Data
US 2022/0258124 A1 Aug. 18, 2022

(30) Foreign Application Priority Data
Jun. 26, 2019 (CN) .......................... 201910560834.0

(51) Int. Cl.
*B01J 20/18* (2006.01)
*B01J 20/28* (2006.01)
(Continued)

(52) U.S. Cl.
CPC ....... *B01J 20/186* (2013.01); *B01J 20/28004* (2013.01); *B01J 20/28035* (2013.01);
(Continued)

(58) Field of Classification Search
CPC .... B01D 15/1807; B01D 15/185; B01J 20/12; B01J 20/18; B01J 20/186; B01J 20/28;
(Continued)

(56) References Cited

U.S. PATENT DOCUMENTS 3,558,732 A 1/1971 Neuzil
3,997,620 A 12/1976 Neuzil et al.
(Continued)

FOREIGN PATENT DOCUMENTS

CN 1275926 A 12/2000
CN 1347339 A 5/2002
(Continued)

OTHER PUBLICATIONS

International Search Report of International Application No. PCT/CN2020/098147, Sep. 17, 2020.

*Primary Examiner* — Brian A McCaig
(74) *Attorney, Agent, or Firm* — FINNEGAN, HENDERSON, FARABOW, GARRETT & DUNNER LLP (57) ABSTRACT

The present invention provides a composite layer agglomerating adsorbent, comprising an outer adsorbent layer containing a low silica X molecular sieve and an inner adsorbent layer containing a high silica X molecular sieve, the low silica X molecular sieve has a silica/alumina molar ratio of 2.07-2.18, the high silica X molecular sieve has a silica/
(Continued)

alumina molar ratio of 2.2-2.5, based on the total amount of the adsorbent, the adsorbent comprises 95.0-100 mass % of the X molecular sieve and 0-5.0 mass % of the matrix, the cation sites of the X molecular sieve in the adsorbent are occupied by a metal of Group IIA or occupied together by a metal of Group IA and a metal of Group IIA. The adsorbent is suitable for the process of adsorptive separation of PX from $C_8$ aromatic hydrocarbons using light aromatic hydrocarbons as desorbent, and has high adsorption selectivity and good mass transfer performance.

17 Claims, 4 Drawing Sheets

(51) Int. Cl.
  B01J 20/30 (2006.01)
  C07C 7/13 (2006.01)
  B01D 15/18 (2006.01)

(52) U.S. Cl.
  CPC ....... B01J 20/3007 (2013.01); B01J 20/3042 (2013.01); B01J 20/3078 (2013.01); B01J 20/3085 (2013.01); C07C 7/13 (2013.01); B01D 15/1807 (2013.01); B01D 15/185 (2013.01); B01J 2220/42 (2013.01); B01J 2220/603 (2013.01)

(58) Field of Classification Search
  CPC ............ B01J 20/28004; B01J 20/28035; B01J 20/30; B01J 20/3007; B01J 20/3042; B01J 20/3078; B01J 20/3085; B01J 2220/42; B01J 2220/4806; B01J 2220/603; C01B 39/22; C07C 7/13; C07C 15/08
  See application file for complete search history.

(56) References Cited

U.S. PATENT DOCUMENTS

| | | | |
|---|---|---|---|
| 2012/0247334 A1* | 10/2012 | Hurst | B01J 20/186 502/67 |
| 2012/0330081 A1 | 12/2012 | Cheng | |
| 2017/0304799 A1* | 10/2017 | Bouvier | B01J 20/28071 |
| 2018/0170834 A1 | 6/2018 | Bjorkman et al. | |

FOREIGN PATENT DOCUMENTS

| | | |
|---|---|---|
| CN | 1565718 A | 1/2005 |
| CN | 101497022 A | 8/2009 |
| CN | 108262004 A | 7/2018 |
| CN | 108525641 A | 9/2018 |
| TW | 201513933 A | 4/2015 |
| WO | WO 2015057280 A1 | 4/2015 |

\* cited by examiner

COMPOSITE LAYER AGGLOMERATING ADSORBENT AND PREPARATION PROCESS THEREOF

CROSS-REFERENCE TO RELATED APPLICATIONS

This application is a national stage filing under 35 U.S.C. § 371 of International Application No. PCT/CN2020/098147, filed Jun. 24, 2020, which claims the priority to and benefits of Chinese Patent Application No. 201910560834.0, filed Jun. 26, 2019, which is incorporated herein by reference.

TECHNICAL FIELD

The present invention relates to an agglomerating adsorbent and a preparation process thereof, in particular to an adsorbent having an X molecular sieve as an active component and a preparation process thereof.

BACKGROUND TECHNOLOGY

Paraxylene (PX) is an important basic chemical raw material, mainly used to produce polyester fibers. At present, adsorptive separation methods are widely used in the industry to separate p-xylene from mixed $C_8$ aromatic hydrocarbons. Adsorptive separation technology includes an adsorbent that can selectively adsorb p-xylene and a continuous countercurrent simulated moving bed adsorptive separation process. Among them, the use of high-performance adsorbents is the key point to obtaining high-purity p-xylene products.

The active component of the p-xylene adsorbent for industrial adsorptive separation is mostly an X molecular sieve. The X molecular sieve and clay are mixed uniformly in a certain proportion, and the adsorbent spheres are obtained by rolling-molding into spheres, drying, calcining and cation exchange. Compression strength, selectivity, adsorption capacity and mass transfer performance are important indices for evaluating adsorbents.

U.S. Pat. No. 3,997,620 found that compared with BaKX, the $Sr^{2+}$ and $Ba^{2+}$ exchanged X molecular sieve has lower selectivity for p-xylene/m-xylene (PX/MX) and p-xylene/o-xylene (PX/OX), but significantly improved selectivity for p-xylene/ethylbenzene (PX/EB) and p-xylene/p-diethylbenzene (PX/PDEB).

CN1275926A discloses an agglomerating zeolite adsorbent, the active component is an X molecular sieve with Si/Al atomic ratio of 1-1.15, and the binder is a zeolitizable clay. After alkali treatment, the clay can be converted into an X molecular sieve so that higher compression strength and adsorption capacity are obtained.

CN1565718A uses a small crystal X molecular sieve with a crystal size of 0.1-0.4 microns as the active component of the adsorbent to improve the mass transfer performance of the adsorbent and increase the adsorption capacity.

CN101497022A discloses an agglomerating adsorbent and a preparation process thereof. In the process, a pore former is added to the mixed powder for preparing the adsorbent, so that a large number of intercrystalline pores with concentrated pore distribution are formed in the adsorbent particles after the transformation, thereby significantly improving the mass transfer performance of the adsorbent.

U.S. Pat. No. 3,558,732 discloses a system for the adsorptive separation of p-xylene from a mixed $C_8$ aromatic hydrocarbon using toluene as desorbent, and the active component of the adsorbent is a BaKX molecular sieve. Compared with the case of benzene as the desorbent, it shows higher adsorption selectivity and product purity.

SUMMARY OF THE INVENTION

The purpose of the present invention is to provide a composite layer agglomerating adsorbent and a preparation process. The adsorbent is suitable for the process of adsorptive separation of PX from $C_8$ aromatic hydrocarbons using light aromatic hydrocarbons as desorbent, and has high adsorption selectivity and good mass transfer performance.

The present invention provides a composite layer agglomerating adsorbent, comprising an outer adsorbent layer containing a low silica X molecular sieve and an inner adsorbent layer containing a high silica X molecular sieve, the low silica X molecular sieve has a silica/alumina molar ratio of 2.07-2.18, the high silica X molecular sieve has a silica/alumina molar ratio of 2.2-2.5, based on the total amount of the adsorbent, the adsorbent comprises 95.0-100 mass % of the X molecular sieve and 0-5.0 mass % of the matrix, the cation sites of the X molecular sieve in the adsorbent are occupied by a metal of Group IIA or occupied together by a metal of Group IA and a metal of Group IIA.

The present invention uses two different X molecular sieves with high and low silica/alumina molar ratios as the active component of the composite layer agglomerating adsorbent, wherein the adsorbent containing a high silica X molecular sieve is placed in the inner layer, and the adsorbent containing a low silica X molecular sieve is placed in the outer layer. The composite layer agglomerating adsorbent is suitable for the adsorptive separation of PX from $C_8$ aromatic hydrocarbons wherein light aromatic hydrocarbons are used as desorbent, and can improve the purity of the separation target product and increase the production capacity of the adsorptive separation apparatus.

DETAILED DESCRIPTION

Any embodiment described herein can be freely combined with one or more other embodiments described herein, and the resulting technical solutions or technical ideas are regarded as part of the original disclosure or the original record of the present invention, and should not be regarded as new content that has not been disclosed or anticipated in this specification, unless those skilled in the art believe that the combination is obviously unreasonable.

In the composite layer agglomerating adsorbent of the present invention, X molecular sieve (also called X-type molecular sieve, X-zeolite or X-type zeolite) is the adsorption active component. Specifically, according to the present invention, a composite layer adsorbent is made by using the adsorbent containing high silica X molecular sieve as the inner layer (hereinafter, sometimes referred to as the inner layer) and using the adsorbent containing low silica X molecular sieve as the outer layer (hereinafter, sometimes also referred to as the outer layer).

In the composite layer agglomerating adsorbent of the present invention, the adsorbent in the outer layer contains X molecular sieve with a low silica/alumina molar ratio (low silica X molecular sieve), which is beneficial to improve the adsorption selectivity of the adsorbent towards p-xylene (PX) relative to ethylbenzene (EB), so that when performing the adsorptive separation, the outer adsorbent can adsorb less ethylbenzene in the adsorbent. On the other hand, the adsorbent in the inner layer contains X molecular sieve with a high silica/alumina molar ratio (high silica X molecular sieve), which can provide higher adsorption selectivity towards para-xylene relative to meta-xylene (MX) and towards para-xylene relative to ortho-xylene (OX), so that the overall performance of the composite layer adsorbent in the adsorptive separation of PX from $C_8$ aromatic hydrocarbons can be improved.

In the adsorbent of the present invention, the content of the X molecular sieve based on the total amount refers to the total content of the X molecular sieves contained in the adsorbent, which includes the high silica X molecular sieve, the low silica X molecular sieve and the X molecular sieve formed after the transformation of kaolin mineral. The matrix content refers to the total amount of the matrices contained in the inner layer and outer layer. In addition, the cation sites of the X molecular sieve refer to all the cation sites in the X molecular sieve contained in the composite layer agglomerating adsorbent.

Optionally, the composite layer agglomerating adsorbent according to the present invention comprises 95.0-99.5 mass % of the X molecular sieve and 0.5-5.0 mass % of the matrix. The composite layer agglomerating adsorbent may further comprise 97.0-99.5 mass % of the X molecular sieve and 0.5-3.0 mass % of the matrix.

In an embodiment of the present invention, the content of the low silica X molecular sieve in the composite layer agglomerating adsorbent is 5-40 mass %, preferably 10-40 mass % of the total amount of the X molecular sieve.

In the present invention, the low silica X molecular sieve in the outer layer has a silica/alumina molar ratio of 2.07-2.18. The low silica X molecular sieve in the outer layer is preferably an X molecular sieve self-agglomerate, which is formed by the aggregation of nano-scale X molecular sieve crystals with small crystal size. The particle size of the self-agglomerate is preferably 1.0-3.0 microns, more preferably 1.0-2.0 microns, and the crystal size of the nano-scale X molecular sieve is preferably 0.1-0.8 nanometers.

In the present invention, the high silica X molecular sieve in the inner layer has a silica/alumina molar ratio of 2.2-2.5, preferably 2.2-2.4. In an embodiment of the present invention, the crystal size of the said high silica X molecular sieve is preferably 0.1-2.5 microns, more preferably 0.5-2.0 microns.

In the present invention, the matrix in the adsorbent is the residue after the transformation of in-situ crystallization of kaolin mineral. The kaolin mineral is selected from at least one of kaolinite, dickite, nacrite, ovenstone and halloysite.

In the adsorbent of the present invention, the cation sites of the X molecular sieve are occupied by a metal of Group IIA or occupied together by a metal of Group IA and a metal of Group IIA. The metal of Group IIA is preferably Ba, and the metal of Group IA is preferably at least one of K, Li and Na. When the cation sites of the X molecular sieve are occupied together by an ion of Ba and an ion of the metal of Group IA, the molar ratio of barium oxide to the oxide of the metal of Group IA (barium oxide/the oxide of the metal of Group IA) is 2-60, preferably 5-46.

The composite layer adsorbent of the present invention is preferably in the shape of small spheres, and the average particle size of the small spheres is preferably 300-850 microns.

The preparation process of the adsorbent of the present invention includes the following steps:

(1) rolling-molding into spheres: mixing a high silica X molecular sieve and a binder uniformly according to the mass ratio of 88-95:5-12, putting them in a turntable and rolling while spraying water to make the solids agglomerate into spheres as the inner core; then adding a powder of a low silica X molecular sieve and a binder mixed according to the mass ratio of 88-95:5-12, continuing to spray water and roll to form the outer layer of spheres, taking spheres with the particle size of 300-850 microns, and drying and then calcining at 500-700° C., (2) In-situ crystallization: taking the spheres calcined in step (1), performing in-situ crystallization treatment with an alkali solution, and then drying, wherein the alkali solution is a mixed solution of sodium hydroxide and potassium hydroxide, the concentration of hydroxide ions in the mixed solution is 0.1-3.0 mol/L, and the molar ratio of $K^+/(Na^++K^+)$ is 0.1-0.6, (3) Ion exchange: cation exchanging the spheres dried in step (2) with a solution of a soluble salt of the metal of Group IIA or with a solution of a soluble salt of the metal of Group IIA and a soluble salt of the metal of Group IA, and then drying and activating.

In the above process, step (1) is to mold the X molecular sieve and the binder by rolling into spheres. Upon rolling into the spheres, the X molecular sieves with different silica/alumina molar ratios are mixed with the binder respectively, and divided into two successive batches to mold by rolling into the spheres. That is, the mixture of the high silica X molecular sieve and the binder is rolled into spheres as the inner core (namely the inner adsorbent layer), and then the mixture of the low silica X molecular sieve and the binder is added and rolled to form the outer layer of the spheres (namely the outer adsorbent layer).

In an embodiment of the present invention, the amount of the low silica X molecular sieve used in rolling-molding into spheres in step (1) is 5-40 mass %, preferably 10-40 mass % of the total amount of the X molecular sieve. The mass ratio of the high silica X molecular sieve to the binder used in step (1) of rolling-molding into spheres is preferably 10-15:1, and the mass ratio of the low silica X molecular sieve to the binder used is preferably 10-15:1.

In an embodiment of the present invention, the binder is kaolin mineral. The kaolin mineral is selected from kaolinite, dickite, nacrite, ovenstone, halloysite or a mixture thereof. The mass fraction of the crystalline substance in the kaolin mineral is at least 90%, preferably 93-99%.

In an embodiment of the present invention, the device for rolling-molding into spheres in step (1) may be a turntable, a coating kettle or a roller. Upon rolling-molding into spheres, the uniformly mixed solid raw materials are put into the rotating device and rolled whiling spraying water to make the solid powder adhere and agglomerate into spheres. Upon rolling into spheres, the addition amount of water is 6-22%, preferably 6-16% of the total mass of the solid.

The spheres obtained after rolling-molding into spheres in step (1) are sieved, and the spheres with a particle size of 300-850 microns are taken, dried, and calcined at 500-700° C. to obtain the adsorbent precursor. The drying temperature is preferably 60-110° C., and the time is preferably 2-12 hours. In an embodiment of the present invention, the calcining temperature is preferably 520-600° C., and the time is preferably 1.0-6.0 hours. After calcining, the kaolin mineral in the spheres is transformed into metakaolin, so as to facilitate the in-situ transformation into X molecular sieve in step (2).

In the above process of the present invention, step (2) is a step of in-situ crystallization of the spheres prepared in step (1), and the alkaline solution used for in-situ crystallization is a mixed solution of sodium hydroxide and potassium hydroxide, wherein the concentration of hydroxyl ions is preferably 0.2-1.6 mol/L, and the molar ratio of $K^+/(Na^+ + K^+)$ is preferably 0.15-0.45.

The liquid/solid ratio for the in-situ crystallization of kaolin mineral with a mixed solution of sodium hydroxide and potassium hydroxide in step (2) is preferably 1.5-5.0 L/kg. The crystallization temperature for in-situ crystallization of kaolin mineral into X-type molecular sieve is preferably 80-100° C., more preferably 85-100° C., and the time is preferably 0.5-8 hours. Spheres after in-situ crystallization are dried, the drying temperature is preferably 60-110° C., and the time is preferably 2-12 hours.

In the above process of the present invention, step (3) is a step of cation-exchanging the spheres dried in step (2). The metal of Group IIA is preferably Ba. The soluble salt of the metal of Group IIA is preferably barium nitrate or barium chloride. The soluble salt of the metal of Group IA is preferably at least one of a nitrate and a chloride thereof. The metal of Group IA is preferably at least one of K, Li and Na.

The cation exchange in step (3) can be performed in a kettle-type or column-type container, preferably in a column-type container for continuous exchange. The temperature for exchanging is preferably 40-120° C., more preferably 85-95° C., the time is preferably 5-25 hours, more preferably 8-16 hours, the liquid hourly space velocity for exchanging is preferably 0.2-10 $hr^{-1}$, more preferably 2-8 $hr^{-1}$.

In an embodiment of the present invention, the composite layer agglomerating adsorbent, in the case of containing both ions selected from the metal of Group IIA and ion selected from the metal of Group IA, the spheres dried in step (2) are simultaneously cation exchanged with a mixed solution of a soluble salt of the metal of Group IIA and a soluble salt of metal of Group IA, or a solution of a soluble salt of the metal of Group IIA and a solution of a soluble salt of metal of Group IA can be respectively prepared, and then the spheres dried in step (2) are respectively cation exchanged either firstly with an ion of metal of Group IIA and then with an ion of metal of Group IA, or firstly with an ion of metal of Group IA and then with an ion of metal of Group IIA.

The spheres cation-exchanged in step (3) are washed, dried and activated to remove sodium ions and water to obtain the composite layer agglomerating adsorbent.

The drying and activation in step (3) can be carried out in flowing hot air or nitrogen. The drying temperature is preferably 40-120° C., more preferably 60-110° C., and the time is preferably 5-60 hours, more preferably 18-40 hours. The activation temperature is preferably 150-250° C., more preferably 160-220° C., and the time is preferably 5-20 hours, more preferably 5-10 hours.

In the present invention, the low silica X molecular sieve is preferably an X molecular sieve self-agglomerate, and its preparation process includes the following steps:

(i) mixing a silicon source, an aluminum source, water and sodium hydroxide according to the molar ratio of $SiO_2/Al_2O_3=2$-25, $Na_2O/Al_2O_3=3$-30, and $H_2O/Al_2O_3=100$-500, and aging the mixture at 0-60° C., preferably 20-50° C. for 1-72 hours to produce a directing agent, (ii) mixing an inorganic base, a potassium source, an aluminum source, a silicon source, the directing agent prepared in step (i) and water uniformly to form a molecular sieve synthesis system, so that the molar ratios of materials in the synthesis system are: $SiO_2/Al_2O_3=2.0$-2.5, $M_2O/SiO_2=1.8$-4.0, $H_2O/SiO_2=40$-96, $K^+/(K^++Na^+)=0.10$-0.65, where M is Na and K, the molar ratio of the amount of $Al_2O_3$ in the directing agent to the total amount of $Al_2O_3$ in the molecular sieve synthesis system is 0.01-2.0%, preferably 0.1-1.0%, (iii) the molecular sieve synthesis system of step (ii) is hydrothermally crystallized at 50-120° C. for 2-72 hours, and the solid obtained after crystallization is washed and dried to obtain an X molecular sieve self-agglomerate.

In step (i) of the above process, preferably the silicon source, the aluminum source, water and sodium hydroxide are mixed according to the molar ratios of $SiO_2/Al_2O_3=8$-21, $Na_2O/Al_2O_3=10$-25, and $H_2O/Al_2O_3=100$-400.

In step (ii) of the above process, the molar ratios of materials in the synthesis system are preferably: $SiO_2/Al_2O_3=2.0$-2.5, $M_2O/SiO_2=2.5$-4.0, and $H_2O/SiO_2=50$-80. $K^+/(K^++Na^+)$ is preferably 0.2-0.5.

The high silica X molecular sieve according to the present invention can be prepared by the conventional process. It is preferably prepared by the following process, which includes the following steps:

(ii-1) mixing an inorganic base, an aluminum source, a silicon source, the directing agent prepared in the above step (i) and water uniformly to form a molecular sieve synthesis system, so that the molar ratios of materials in the synthesis system are: $SiO_2/Al_2O_3=2.5$-3.0, $Na_2O/SiO_2=0.7$-1.8, $H_2O/SiO_2=40$-96, where the molar ratio of the amount of $Al_2O_3$ in the directing agent to the total amount of $Al_2O_3$ in the molecular sieve synthesis system is 0.01-2.0%, preferably 0.1-1.0%, (iii-1) the molecular sieve synthesis system of step (ii-1) is hydrothermally crystallized at 50-120° C. for 2-72 hours, and the solid obtained after crystallization is washed and dried to obtain a high silica X molecular sieve according to the present invention.

In the above process for preparing the X molecular sieve, the aluminum source used for synthesizing the molecular sieve can be selected from at least one of low alkalinity sodium metaaluminate, alumina, aluminum hydroxide, aluminum sulfate, aluminum chloride, aluminum nitrate and sodium aluminate. The $Na_2O$ content in the low alkalinity sodium metaaluminate is 7.6-23.7 mass %, preferably 8-14 mass %, and the $Al_2O_3$ content is preferably 7.0-15.0 mass %.

In the above process for preparing the X molecular sieve, the potassium source used for synthesizing the molecular sieve is selected from at least one of potassium hydroxide, potassium fluoride, potassium chloride, potassium bromide, potassium iodide, potassium carbonate, potassium nitrate and potassium sulfate.

In the above process for preparing the X molecular sieve, the silicon source used for synthesizing the molecular sieve is selected from at least one of ethyl orthosilicate, silica sol, water glass, sodium silicate, silica gel and white carbon black.

In the above process for preparing the X molecular sieve, the inorganic base is preferably sodium hydroxide.

In the above process for preparing the X molecular sieve, the temperature for hydrothermal crystallization of the molecular sieve synthesis system is preferably 70-110° C., more preferably 80-100° C., and the time is preferably 3-24 hours.

The composite layer adsorbent provided by the present invention is suitable for liquid-phase adsorptive separation of p-xylene from $C_8$ aromatic hydrocarbons, and the desorbent used for the adsorptive separation is preferably toluene. The liquid-phase adsorptive separation can be performed in a plurality of columns connected in series, or in a simulated moving bed realized by means of a rotary valve or a solenoid valve group. The operating pressure of the adsorptive separation is 0.3-1.5 MPa, and the operating temperature is 120-180° C.

Three important indicators to evaluation the performance of adsorbents are adsorption capacity, selectivity, and the adsorption rate and desorption rate of the target product to be separated (such as p-xylene).

In order to evaluate the adsorption performance of the adsorbent, a dynamic pulse experimental device can be used to determine the adsorption selectivity of the adsorbent and the adsorption rate and desorption rate of the target product to be separated. The device comprises a feed system, an adsorption column, a heating furnace, a pressure control valve, and the like. The adsorption column is a 0 6×1800 mm stainless steel tube. An inlet at the lower end of the adsorption column is connected with a feed and nitrogen system, and an outlet at the upper end is connected with the pressure control valve, and then connected to an effluent collector.

The method for determining the adsorption selectivity of the adsorbent is as follows: loading the weighed adsorbent particles with a particle size of 300-850 μm to be measured into the adsorption column and compacting same, activating by dehydrating in a nitrogen atmosphere at 160-190° C.; and then passing through the desorbent to remove the gas in the system. The system pressure is raised to 0.8 MPa, the temperature is raised to 145° C., the introduction of the desorbent is stopped, 8 mL of a pulse feed solution is introduced at a volumetric space velocity of 1.0 hr$^{-1}$, the feed solution contains an unadsorbable tracer, then the desorbent is introduced at the same volumetric space velocity, and 3 drops of the desorbent sample is taken every 2 minutes, and analyzed by gas chromatography. The volume of the desorbent for desorption is used as the abscissa, the concentration of each component of the pulse feed solution is used as the ordinate, and the desorption curve of each component of the pulse feed solution is plotted. Among others, the unadsorbable tracer can be used to obtain the dead volume of the adsorption system. The midpoint of the half-peak width of the tracer is taken as a zero point, and the net retention volume R from the midpoint of the half-peak width to the zero point of each component is determined; the net retention volume of any component is directly proportional to the partition coefficient at the adsorption equilibrium, reflecting the force between each component and the adsorbent; the ratio of the net retention volumes of the two components is the selectivity β, for example, the ratio of the net retention volume of PX to the net retention volume of EB is the ratio of the adsorption performance of the adsorbent for PX to the adsorption performance of the adsorbent for EB, and is the adsorption selectivity of PX relative to EB, which is recorded as $\beta_{P/E}$; the ratio of the net retention volume of PX to the net retention volume of MX is the ratio of the adsorption performance of the adsorbent for PX to the adsorption performance of the adsorbent for MX, and is the adsorption selectivity of PX relative to MX, which is recorded as $\beta_{P/M}$; and the ratio of the net retention volume of PX to the net retention volume of OX is the ratio of the adsorption performance of the adsorbent for PX to the adsorption performance of the adsorbent for OX, and is the adsorption selectivity of PX relative to OX, which is recorded as $\beta_{P/O}$.

To represent the PX adsorption rate and the desorption rate, and the adsorption selectivity between PX and T (toluene), the adsorption rate $[SA]_{10\text{-}90}$ and the desorption rate $[SD]_{90\text{-}10}$ of PX are introduced. The adsorption rate $[SA]_{10\text{-}90}$ is the volume of the desorbent required for the PX concentration in the PX pulse desorption curve to rise from 10% to 90%, and the desorption rate $[SD]_{90\text{-}10}$ is the volume of the desorbent required for the PX concentration in the desorption curve to decrease from 90% to 10%, and the $[SA]_{10\text{-}90}/[SD]_{90\text{-}10}$ ratio is defined as the adsorption selectivity $\beta_{PX/T}$ between PX and the desorbent.

The following examples will further illustrate the present invention, but the present invention is not limited thereto.

In the example, the toluene gas phase adsorption experiment is used to determine the adsorption capacity of the adsorbent. The specific operation process is as follows: the nitrogen carrying toluene (the partial pressure of toluene is 0.5 MPa) is contacted with a certain mass of the adsorbent at 35° C., until toluene reaches the adsorption equilibrium. According to the mass difference of the adsorbent before and after the adsorption of toluene, the adsorption capacity of the tested adsorbent is calculated from the following formula.

$$C = \frac{m_2 - m_1}{m_1} \times 1000$$

wherein, C is the adsorption capacity, the unit is mg/g; $m_1$ is the mass of the tested adsorbent before the adsorption of toluene, the unit is gram; and $m_2$ is the mass of the tested adsorbent after the adsorption of toluene, the unit is gram.

The method to determine the adsorption performance of the adsorbent: 50 grams of the adsorbent is subjected to a liquid phase pulse experiment to measure the adsorption selectivity and the adsorption rate and desorption rate of PX. The desorbent used in the experiment is 30% by volume of toluene (T) and 70% by volume of n-heptane. The composition of the pulse feed solution is ethylbenzene (EB), p-xylene (PX), m-xylene (MX), o-xylene (OX), and n-nonane (NC9), each accounting for 5 vol %, and 75 vol % of the desorbent, where n-nonane is the tracer.

Example 1

The following examples are to prepare the low silica X molecular sieve of the present invention.
(1) Preparation of the Directing Agent 4.02 kg of sodium hydroxide, 7.81 kg of deionized water, 5.32 kg of low alkalinity sodium aluminate solution (having an $Al_2O_3$ content of 9.99 mass % and a $Na_2O$ content of 10.93 mass %, hereinafter the same), and 23.24 kg of water glass (having a $SiO_2$ content of 20.17 mass % and a $Na_2O$ content of 6.32 mass %, hereinafter the same) were added to the reactor, stirred and mixed uniformly, and allowed to stand and age for 24 hours at 35° C. to obtain a directing agent. The molar ratios of various materials in the directing agent were $SiO_2/Al_2O_3=15$, $Na_2O/Al_2O_3=16$, $H_2O/Al_2O_3=320$.

(2) Preparation of the Low Silica X Molecular Sieve 7.50 kg of sodium hydroxide, 8.67 kg of potassium hydroxide, 51.59 kg of deionized water, 35.16 kg of low-alkalinity sodium metaaluminate solution, 23.30 kg of water glass and 0.54 kg of the directing agent prepared in step (1) were added into the reactor, stirred and mixed uniformly to form a molecular sieve synthesis system. The total molar ratios of various materials in the molecular sieve synthesis system were: $SiO_2/Al_2O_3=2.30$, $M_2O/SiO_2=3.25$, $H_2O/SiO_2=70$, where M was K and Na, $K^+/(K^++Na^+)=0.30$, the molar ratio of the amount of $Al_2O_3$ in the added directing agent to the total $Al_2O_3$ in the molecular sieve synthesis system was 0.2%.

Figure 1:
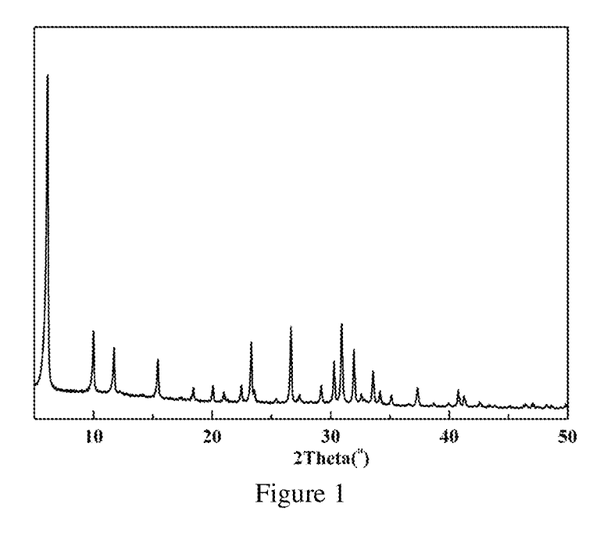
FIG. 1 is an X-ray diffraction (XRD) pattern of the low silica X molecular sieve prepared in Example 1.
Figure 2:
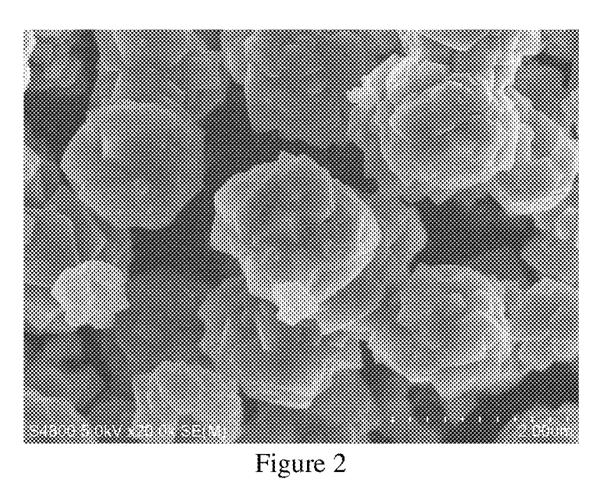
FIG. 2 is a scanning electron microscope (SEM) photo of the low silica X molecular sieve prepared in Example 1.

The above-mentioned molecular sieve synthesis system was continuously stirred for half an hour to form a milky white sol, which was transferred to a reactor, hydrothermally crystallized at 95° C. for 12 hours, and filtered. The resulting solid was washed with deionized water until the filtrate had a pH of 8-9, and dried at 80° C. for 12 hours to obtain a low silica X molecular sieve a, the XRD pattern of which was shown in FIG. 1, demonstrating a net X molecular sieve, the scanning electron micrograph (SEM) of which was shown in FIG. 2, demonstrating that the low silica X zeolite was a self-agglomerate of the X molecular sieve crystal grains, the particle size of the self-agglomerate was 1.4 microns, the crystal grain size of the X molecular sieve in the self-agglomerate was 0.6 nanometers, and the silica/alumina molar ratio of which measured by the X-ray fluorescence spectroscopy (XRF) was 2.09.

Example 2

The low silica X molecular sieve was prepared according to the process of Example 1, except that in step (2) 5.84 kg of sodium hydroxide, 11.56 kg of potassium hydroxide, 53.73 kg of deionized water, 32.35 kg of low alkalinity sodium metaaluminate solution, 23.33 kg of water glass and 0.49 kg of the directing agent prepared in step (1) were added into the reactor, stirred and mixed uniformly to form a molecular sieve synthesis system. The total molar ratios of various materials in the molecular sieve synthesis system were: $SiO_2/Al_2O_3=2.50$, $M_2O/SiO_2=3.25$, $H_2O/SiO_2=70$, where M was K and Na, $K^+/(K^++Na^+)=0.40$, the molar ratio of the amount of $Al_2O_3$ in the added directing agent to the total $Al_2O_3$ in the molecular sieve synthesis system was 0.2%.

Figure 3:
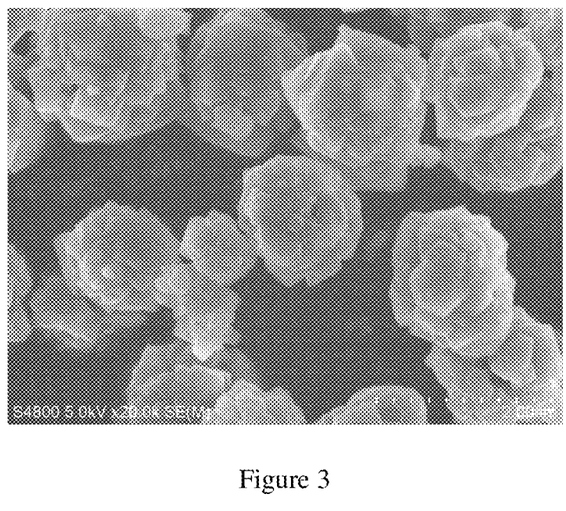
FIG. 3 is an SEM image of the low silica X molecular sieve prepared in Example 2.

The above-mentioned molecular sieve synthesis system was hydrothermally crystallized, filtered, washed, and dried to obtain a low silica X molecular sieve c, the XRD of which demonstrated a net X molecular sieve, the scanning electron micrograph (SEM) of which was shown in FIG. 3, demonstrating that the low silica X zeolite was a self-agglomerate of the X molecular sieve crystal grains, the particle size of the self-agglomerate was 1.3 microns, the crystal grain size of the X molecular sieve in the self-agglomerate was 0.5 nanometers, and the silica/alumina molar ratio of which measured by XRF was 2.16.

Example 3

Preparation of the High Silica X Molecular Sieve of the Present Invention 1.07 kg of sodium hydroxide, 58.40 kg of deionized water, 30.18 kg of low-alkalinity sodium metaaluminate solution, 23.34 kg of water glass and 0.46 kg of the directing agent prepared in step (1) of Example 1 were added into the reactor, stirred and mixed uniformly to form a molecular sieve synthesis system. The total molar ratios of various materials in the molecular sieve synthesis system were: $SiO_2/Al_2O_3=2.70$, $Na_2O/SiO_2=1.25$, $H_2O/SiO_2=70$, the molar ratio of the amount of $Al_2O_3$ in the added directing agent to the total $Al_2O_3$ in the molecular sieve synthesis system was 0.2%.

Figure 4:
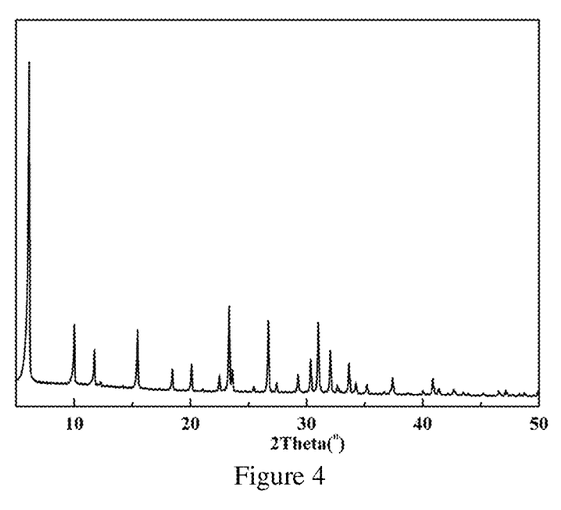
FIG. 4 is an XRD pattern of the high silica X molecular sieve prepared in Example 3.
Figure 5:
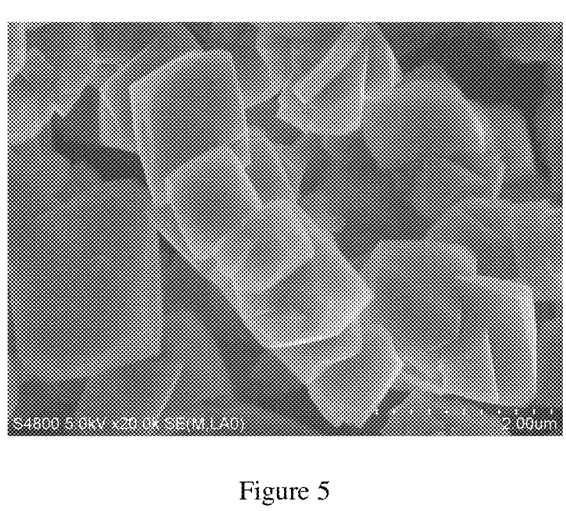
FIG. 5 is an SEM image of the high silica X molecular sieve prepared in Example 3.

The above-mentioned molecular sieve synthesis system was continuously stirred for half an hour to form a milky white sol, which was transferred to a reactor, hydrothermally crystallized at 95° C. for 12 hours, and filtered. The resulting solid was washed with deionized water until the filtrate had a pH of 8-9, and dried at 80° C. for 12 hours to obtain a high silica X molecular sieve b, the XRD pattern of which was shown in FIG. 4, demonstrating a net X molecular sieve, the scanning electron micrograph (SEM) of which was shown in FIG. 5, demonstrating that its crystal grain size was 1.0 micrometer, substantially free of the formation of the self-agglomerate, and the silica/alumina molar ratio measured by XRF was 2.26.

Example 4

Preparation of the Composite Layer Adsorbent of the Present Invention (1) rolling-molding into spheres: 88 kg (the calcined-based mass, hereinafter the same) of the high silica X molecular sieve b produced in Example 3 and 6.62 kg of kaolin (the crystalline substance content of 90 mass %, hereinafter the same) were mixed uniformly to obtain a mixture I, and 5 kg of the low silica X molecular sieve a prepared in Example 1 and 0.38 kg of kaolin were mixed uniformly to obtain a mixture II. The mixture I was put into the turntable and rolled while an appropriate amount of deionized water was sprayed to make the solid powders agglomerate into spheres as the inner core; then the mixture II was added, water was continuously sprayed, and the mixture was molded by rolling to form the outer layer of spheres. The amount of water sprayed during rolling was 8 mass % of the total amount of the solid powder. The spheres were sieved, and the spheres with a particle size of 300-850 microns were taken, dried at 80° C. for 10 hours, and calcined at 540° C. for 4 hours.

(2) In-situ crystallization: 64 kg of spheres calcined in step (1) were placed in 200 liters of a mixed solution of sodium hydroxide and potassium hydroxide, the concentration of hydroxide ions in the mixed solution was 0.3 mol/L, the molar ratio of $K^+/(Na^++K^+)$ was 0.2, the in-situ crystallization treatment was carried out at 95° C. for 4 hours, the solid after crystallization was washed with water until the pH of the washing liquid was less than 10, and dried at 80° C. for 10 hours.

(3) Ion exchanging: 130 mL of the spheres dried in step (2) was loaded into an ion-exchange column to perform the cation exchanging. A continuous exchanging was continuously carried out with a mixed solution of 0.18 mol/L of barium nitrate and 0.07 mol/L of potassium chloride at a volumetric space velocity of 6.0 $hr^{-1}$, 0.1 MPa and 94° C. for 8 hours, and the total amount of the mixed solution was 5000 mL. After the ion-exchanging was completed, the solid was washed at 70° C. with 700 mL of deionized water, dried at 70° C. under a nitrogen atmosphere for 30 hours, dehydrated and activated under a nitrogen atmosphere at 180° C. for 6 hours to obtain an adsorbent A, the inner layer thereof was an inner adsorbent layer containing a high silica X molecular sieve, and the outer layer was an outer adsorbent layer containing a low silica X molecular sieve, wherein the content of the X molecular sieve was 98.6 mass %, the content of the matrix was 1.4 mass %, and the molar ratio of BaO to K2O in the adsorbent was 36.

1.0 g of the adsorbent A was taken to determine its toluene adsorption capacity, and the result was shown in Table 1.

50 g of the adsorbent A was subjected to a liquid phase pulse experiment to determine its adsorption selectivity and the adsorption rate and desorption rate of PX. The determined adsorption performance was shown in Table 1.

Example 5

The composite layer adsorbent was prepared according to the process of Example 4, except that in step (1), 78 kg of the high silica X molecular sieve b prepared in Example 3 and 5.87 kg of kaolin were mixed uniformly to make the mixture I, 15 kg of the low silica X molecular sieve a prepared in Example 1 and 1.13 kg of kaolin were mixed uniformly to make the mixture II. The adsorbent B was obtained by rolling-molding into spheres, in-situ crystallization and ion exchange. Its inner layer was an inner adsorbent layer containing a high silica X molecular sieve, and the outer layer was an outer adsorbent layer containing a low silica X molecular sieve, wherein the content of the X molecular sieve was 98.4 mass % and the content of the matrix was 1.6 mass %. 1 g and 50 g of the adsorbents B were respectively taken to determine the toluene adsorption capacity and the adsorption performance. The results were shown in Table 1.

Example 6

The composite layer adsorbent was prepared according to the process of Example 4, except that in step (1), 68 kg of the high silica X molecular sieve b prepared in Example 3 and 5.13 kg of kaolin were mixed uniformly to make the mixture I, 25 kg of the low silica X molecular sieve a prepared in Example 1 and 1.87 kg of kaolin were mixed uniformly to make the mixture II. The adsorbent C was obtained by rolling-molding into spheres, in-situ crystallization and ion exchange. Its inner layer was an inner adsorbent layer containing a high silica X molecular sieve, and the outer layer was an outer adsorbent layer containing a low silica X molecular sieve, wherein the content of the X molecular sieve was 98.5 mass % and the content of the matrix was 1.5 mass %. 1 g and 50 g of the adsorbents C were respectively taken to determine the toluene adsorption capacity and the adsorption performance. The results were shown in Table 1.

Example 7

The composite layer adsorbent was prepared according to the process of Example 4, except that in step (1), 78 kg of the high silica X molecular sieve b prepared in Example 3 and 5.87 kg of kaolin were mixed uniformly to make the mixture I, 15 kg of the low silica X molecular sieve c prepared in Example 2 and 1.13 kg of kaolin were mixed uniformly to make the mixture II. The adsorbent D was obtained by rolling-molding into spheres, in-situ crystallization and ion exchange. Its inner layer was an inner adsorbent layer containing a high silica X molecular sieve, and the outer layer was an outer adsorbent layer containing a low silica X molecular sieve, wherein the content of the X molecular sieve was 97.9 mass % and the content of the matrix was 2.1 mass %. 1 g and 50 g of the adsorbents D were respectively taken to determine the toluene adsorption capacity and the adsorption performance. The results were shown in Table 1.

Example 8

The composite layer adsorbent was prepared according to the process of Example 4, except that in step (1), 68 kg of the high silica X molecular sieve b prepared in Example 3 and 5.13 kg of kaolin were mixed uniformly to make the mixture I, 25 kg of the low silica X molecular sieve c prepared in Example 2 and 1.87 kg of kaolin were mixed uniformly to make the mixture II. The adsorbent E was obtained by rolling-molding into spheres, in-situ crystallization and ion exchange. Its inner layer was an inner adsorbent layer containing a high silica X molecular sieve, and the outer layer was an outer adsorbent layer containing a low silica X molecular sieve, wherein the content of the X molecular sieve was 98.0 mass % and the content of the matrix was 2.0 mass %. 1 g and 50 g of the adsorbents E were respectively taken to determine the toluene adsorption capacity and the adsorption performance. The results were shown in Table 1.

Example 9

The composite layer adsorbent was prepared according to the process of Example 4, except that in step (1), 58 kg of the high silica X molecular sieve b prepared in Example 3 and 4.37 kg of kaolin were mixed uniformly to make the mixture I, 35 kg of the low silica X molecular sieve c prepared in Example 2 and 2.63 kg of kaolin were mixed uniformly to make the mixture II. The adsorbent F was obtained by rolling-molding into spheres, in-situ crystallization and ion exchange. Its inner layer was an inner adsorbent layer containing a high silica X molecular sieve, and the outer layer was an outer adsorbent layer containing a low silica X molecular sieve, wherein the content of the X molecular sieve was 98.2 mass % and the content of the matrix was 1.8 mass %. 1 g and 50 g of the adsorbents F were respectively taken to determine the toluene adsorption capacity and the adsorption performance. The results were shown in Table 1.

Comparative Example 1

93 kg of the low silica X molecular sieve a prepared in Example 1 and 7 kg of kaolin were mixed uniformly, put into the turntable and rolled while an appropriate amount of deionized water was sprayed to make the solid powders agglomerate into spheres. The amount of water sprayed during rolling into spheres was 8 mass % of the total amount of the solid powder. The spheres were sieved, and the spheres with a particle size of 300-850 microns were taken, dried at 80° C. for 10 hours, and calcined at 540° C. for 4 hours. Then the in-situ crystallization and the ion exchange were performed according to step (2) and step (3) of Example 4 to obtain an adsorbent G, wherein the content of the X molecular sieve was 98.3 mass % and the content of the matrix was 1.7 mass % respectively. 1 g and 50 g of the adsorbents G were taken to determine the toluene adsorption capacity and the adsorption performance. The results were shown in Table 1.

Comparative Example 2

The adsorbent was prepared according to the process of Comparative Example 1, except that 93 kg of the high silica X molecular sieve b prepared in Example 3 and 7 kg of kaolin were mixed uniformly, and the adsorbent H was obtained by rolling-molding into spheres, in-situ crystallization and ion exchange, wherein the content of the X molecular sieve was 97.5 mass %, and the content of the matrix was 2.5 mass %. 1 g and 50 g of the adsorbents H were taken to determine the toluene adsorption capacity and the adsorption performance. The results were shown in Table 1.

Comparative Example 3

25 kg of the low silica X molecular sieve a prepared in Example 1, 68 kg of the high silica X molecular sieve b prepared in Example 3, and 7 kg of kaolin were mixed uniformly, put into the turntable and rolled while an appropriate amount of deionized water was sprayed to make the solid powders agglomerate into spheres. The amount of water sprayed during rolling into spheres was 8 mass % of the total amount of the solid powder. The spheres were sieved, and the spheres with a particle size of 300-850 microns were taken, dried at 80° C. for 10 hours, and calcined at 540° C. for 4 hours. Then the in-situ crystallization and the ion exchange were performed according to step (2) and step (3) of Example 4 to obtain an adsorbent I, wherein the content of the X molecular sieve was 98.5 mass % and the content of the matrix was 1.5 mass % respectively. 1 g and 50 g of the adsorbents I were taken to determine the toluene adsorption capacity and the adsorption performance. The results were shown in Table 1.

Comparative Example 4

An adsorbent was prepared according to the process of Comparative Example 3, except that 25 kg of the low silica X molecular sieve c prepared in Example 2 was used instead of the low silica X molecular sieve a to obtain an adsorbent J, wherein the content of the X molecular sieve was 98.0 mass % and the content of the matrix was 2.0 mass %. 1 g and 50 g of the adsorbents J were taken to determine the toluene adsorption capacity and the adsorption performance. The results were shown in Table 1.

Example 10

An experiment of separating p-xylene with the adsorbent A was performed on a small-scale simulated moving bed with continuous countercurrent flow.

Figure 6:
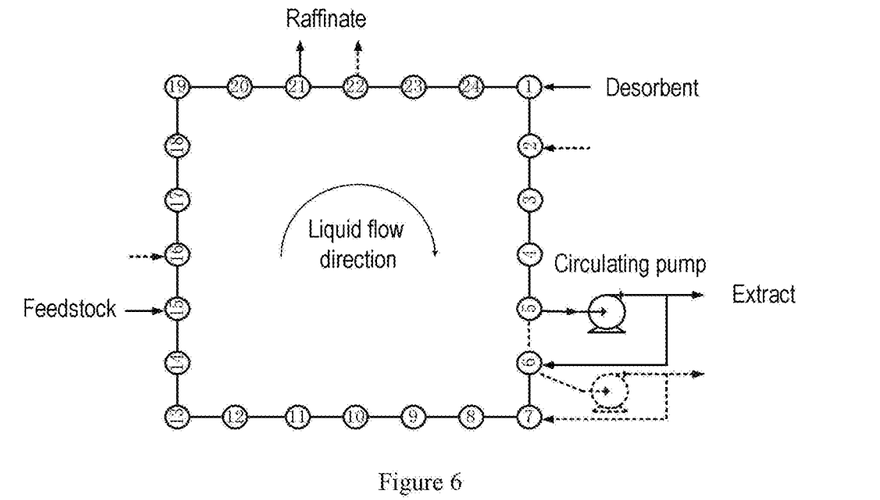
FIG. 6 is a schematic diagram of the adsorptive separation in a small-scale simulated moving bed.

The small-scale simulated moving bed apparatus included 24 adsorption columns connected in series, each with a length of 195 mm and an inner diameter of 30 mm. The total loading amount of the adsorbent was 3300 mL. The head end and the tail end of the 24 columns connected in series were connected by a circulating pump to form a closed loop, as shown in FIG. 6. Four incoming or outgoing streams, namely an adsorption feedstock, a desorbent, an extract, and a raffinate divided 24 adsorption columns into four zones, namely 7 adsorption columns between the adsorption feedstock (column 15) and the raffinate (column 21) formed an adsorption zone, 9 adsorption columns between the extract (column 6) and the adsorption feedstock (column 14) formed a purification zone, and 5 adsorption columns between the desorbent (column 1) and the extract (column 5) formed a desorption zone, and 3 adsorption columns between the raffinate (column 22) and the desorbent (column 24) formed a buffer zone. The temperature of the entire adsorption system was controlled at 145° C., and the pressure was 0.8 MPa.

During the operation, the desorbent toluene and the feedstock were continuously injected into the simulated moving bed at the flow rates of 2118 mL/hour and 1925 mL/hour, respectively, and the extract and the raffinate were withdrawn from the simulated moving bed at the flow rates of 1540 mL/hour and 2503 mL/hour respectively. The feedstock composition is: ethylbenzene 9.3 mass %, p-xylene 18.5 mass %, meta-xylene 45.5 mass %, o-xylene 17.4 mass %, and non-aromatic component 9.3 mass %.

The flow rate of the circulating pump was set to 4890 mL/h, and four streams moved simultaneously by one adsorption column in the same direction as the liquid flow every 80 seconds (in FIG. 6, from the solid line to the dotted line, the rest can be deduced accordingly). Under stable operating conditions, the purity of p-xylene obtained with the adsorbent A was 99.80 mass %, and the yield was 98.53 mass %.

Example 11

A small-scale simulated moving bed apparatus was loaded with the adsorbent B, and an experiment for the adsorptive separation of p-xylene was carried out according to the process of Example 10. The purity of p-xylene obtained under stable operating conditions was 99.80 mass %, and the yield was 98.95 mass %.

Comparative Example 5

A small-scale simulated moving bed apparatus was loaded with the comparative adsorbent G, and an experiment for the adsorptive separation of p-xylene was carried out according to the process of Example 10. The purity of p-xylene obtained under stable operating conditions was 98.71 mass %, and the yield was 97.55 mass %.

Comparative Example 6

A small-scale simulated moving bed apparatus was loaded with the comparative adsorbent H, and an experiment for the adsorptive separation of p-xylene was carried out according to the process of Example 10. The purity of p-xylene obtained under stable operating conditions was 98.86 mass %, and the yield was 97.43 mass %.

Comparative Example 7

A small-scale simulated moving bed apparatus was loaded with the comparative adsorbent I, and an experiment for the adsorptive separation of p-xylene was carried out according to the process of Example 10. The purity of p-xylene obtained under stable operating conditions was 99.26 mass %, and the yield was 98.05 mass %.

Comparative Example 8

A small-scale simulated moving bed apparatus was loaded with the comparative adsorbent J, and an experiment for the adsorptive separation of p-xylene was carried out according to the process of Example 10. The purity of p-xylene obtained under stable operating conditions was 99.10 mass %, and the yield was 98.01 mass %.

TABLE 1

| Example No. | Adsorbent No. | Adsorption capacity, mg/g | Adsorption selectivity $\beta_{P/E}$ | $\beta_{P/M}$ | $\beta_{P/O}$ | $[SA]_{10\text{-}90}$, mL | $[SD]_{90\text{-}10}$, mL | $\beta_{PX/T}$ |
|---|---|---|---|---|---|---|---|---|
| 4 | A | 168 | 2.03 | 3.34 | 2.92 | 15.76 | 16.06 | 0.981 |
| 5 | B | 165 | 2.06 | 3.39 | 2.97 | 15.86 | 16.17 | 0.981 |
| 6 | C | 162 | 2.10 | 3.46 | 3.03 | 15.90 | 16.21 | 0.981 |
| 7 | D | 172 | 1.99 | 3.32 | 2.91 | 15.56 | 15.90 | 0.979 |
| 8 | E | 170 | 2.00 | 3.35 | 2.94 | 15.60 | 15.92 | 0.980 |
| 9 | F | 169 | 2.04 | 3.40 | 2.98 | 15.66 | 16.03 | 0.977 |
| Comp. Ex. 1 | G | 158 | 2.10 | 3.12 | 2.75 | 15.98 | 16.31 | 0.980 |
| Comp. Ex. 2 | H | 173 | 1.96 | 3.36 | 2.94 | 15.69 | 16.00 | 0.981 |
| Comp. Ex. 3 | I | 162 | 2.05 | 3.26 | 2.81 | 15.93 | 16.25 | 0.980 |
| Comp. Ex. 4 | J | 170 | 1.97 | 3.29 | 2.84 | 15.64 | 15.95 | 0.981 |

The invention claimed is:

1. A composite layer agglomerating adsorbent, comprising an outer adsorbent layer containing a low silica X molecular sieve and an inner adsorbent layer containing a high silica X molecular sieve, the low silica X molecular sieve has a silica/alumina molar ratio of 2.07-2.18, the high silica X molecular sieve has a silica/alumina molar ratio of 2.2-2.5, based on the total amount of the adsorbent, the adsorbent comprises 95.0-100 mass % of the X molecular sieve and 0-5.0 mass % of a matrix, the cation sites of the X molecular sieve in the adsorbent are occupied by a metal of Group IIA or occupied together by a metal of Group IA and a metal of Group IIA.

2. The adsorbent according to claim 1, characterized in that the adsorbent comprises 95.0-99.5 mass % of the X molecular sieve and 0.5-5.0 mass % of the matrix.

3. The adsorbent according to claim 1, characterized in that the content of the low silica X molecular sieve in the adsorbent is 5-40 mass % of the total amount of the X molecular sieve.

4. The adsorbent according to claim 1, characterized in that the low silica X molecular sieve is a nano X molecular sieve self-agglomerate, and the particle size of the X molecular sieve self-agglomerate is 1.0-3.0 microns, and the crystal size of the nano X molecular sieve is 0.1-0.8 nanometers.

5. The adsorbent according to claim 1, characterized in that the crystal size of said high silica X molecular sieve is 0.1-2.5 microns.

6. The adsorbent according to claim 1, characterized in that the metal of Group IIA is Ba, and the metal of Group IA is at least one of K, Li and Na.

7. The adsorbent according to claim 1, characterized in that the matrix is the residue after the transformation by in-situ crystallization of kaolin mineral.

8. The adsorbent according to claim 7, characterized in that the kaolin mineral is selected from at least one of kaolinite, dickite, nacrite, ovenstone and halloysite.

9. A process for preparing the adsorbent according to claim 1, comprising the following steps:
  (1) rolling-molding into spheres: mixing a high silica X molecular sieve and a binder uniformly according to the mass ratio of 88-95:5-12, putting them in a turntable and rolling while spraying water to make the solids agglomerate into spheres as the inner core; then adding a powder of a low silica X molecular sieve and a binder mixed according to the mass ratio of 88-95:5-12, continuing to spray water and roll to form the outer layer of spheres, taking spheres with the particle size of 300-850 microns, and drying and then calcining at 500-700° C.,
  (2) in-situ crystallization: taking the spheres calcined in step (1), performing in-situ crystallization treatment with an alkali solution, and then drying, wherein the alkali solution is a mixed solution of sodium hydroxide and potassium hydroxide, the concentration of hydroxide ions in the mixed solution is 0.1-3.0 mol/L, and the molar ratio of $K^+/(Na^++K^+)$ is 0.1-0.6,
  (3) ion exchange: cation exchanging the spheres dried in step (2) with a solution of a soluble salt of the metal of Group IIA or with a solution of a soluble salt of the metal of Group IIA and a soluble salt of the metal of Group IA, and then drying and activating.

10. The process according to claim 9, characterized in that in step (1), upon rolling into spheres, the addition amount of water is 6-22 mass % of the total amount of the powder of the low silica X molecular sieve.

11. The process according to claim 9, characterized in that in step (1), the low silica X molecular sieve in the total amount of the X molecular sieve is 5-40 mass %.

12. The process according to claim 9, characterized in that the temperature for the in-situ crystallization with the alkali solution is 80-100° C.

13. The process according to claim 9, characterized in that in step (3), the spheres dried in step (2) are cation exchanged with a mixed solution of a soluble salt of the metal of Group IIA and a soluble salt of metal of Group IA, or the spheres dried in step (2) are cation exchanged respectively with a solution of a soluble salt of the metal of IIA or a solution of a soluble salt of metal of Group IA.

14. The process according to claim 9, characterized in that the soluble salt of the metal of Group IIA is selected from barium nitrate or barium chloride, and the soluble salt of the metal of Group IA is selected from at least one of a nitrate and a chloride thereof.

15. The process according to claim 14, characterized in that the metal of Group IA is at least one of K, Li and Na.

16. The process according to claim 9, characterized in that the low silica X molecular sieve is an X molecular sieve self-agglomerate, and its preparation process includes the following steps:
  (i) mixing a silicon source, an aluminum source, water and sodium hydroxide according to the molar ratio of $SiO_2/Al_2O_3$=2-25, $Na_2O/Al_2O_3$=3-30, and $H_2O/$ $Al_2O_3$=100-500, and aging the mixture at 0-60° C. for 1-72 hours to produce a directing agent, (ii) mixing an inorganic base, a potassium source, an aluminum source, a silicon source, the directing agent prepared in step (i) and water uniformly to form a molecular sieve synthesis system, so that the molar ratios of materials in the synthesis system are: $SiO_2/Al_2O_3$=2.0-2.5, $M_2O/SiO_2$=1.8-4.0, $H_2O/SiO_2$=40-96, $K^+/(K^++Na^+)$=0.10-0.65, where M is Na and K, the molar ratio of the amount of $Al_2O_3$ in the directing agent to the total amount of $Al_2O_3$ in the molecular sieve synthesis system is 0.01-2.0%, (iii) the molecular sieve synthesis system of step (ii) is hydrothermally crystallized at 50-120° C. for 2-72 hours, and the solid obtained after crystallization is washed and dried to obtain an X molecular sieve self-agglomerate.

17. The process according to claim 16, characterized in that the aluminum source is at least one selected from low alkalinity sodium metaaluminate, alumina, aluminum hydroxide, aluminum sulfate, aluminum chloride, aluminum nitrate and sodium aluminate, wherein the low alkalinity sodium metaaluminate is an alkalinity sodium metaaluminate having the $Na_2O$ content of 7.6-23.7 mass %, and the $Al_2O_3$ content of 7.0-15.0 mass %.

\* \* \* \* \*